United States Patent [19]

Marsh

[11] Patent Number: 5,471,405
[45] Date of Patent: Nov. 28, 1995

[54] APPARATUS FOR MEASUREMENT OF FORCES AND PRESSURES APPLIED TO A GARMENT

[76] Inventor: Stephen A. Marsh, 21 Payson Estate, 456 Belmont St., Watertown, Mass. 02172

[21] Appl. No.: 272,928

[22] Filed: Jul. 11, 1994

Related U.S. Application Data

[63] Continuation of Ser. No. 975,854, Nov. 13, 1992, abandoned.

[51] Int. Cl.$^6$ .............................. G01L 1/00; G01L 5/16; A43B 5/00
[52] U.S. Cl. ..................... 364/556; 364/550; 73/172; 128/774; 128/779; 36/114
[58] Field of Search ..................... 128/774, 779; 73/172; 273/454; 364/550, 556, 558, 561; 341/20, 29; 36/114, 115, 132, 136, 137

[56] References Cited

U.S. PATENT DOCUMENTS

| | | | |
|---|---|---|---|
| 2,290,387 | 7/1942 | Schwartz | 128/779 |
| 4,267,728 | 5/1981 | Manley et al. | 73/172 |
| 4,453,267 | 6/1984 | Paganini et al. | 382/29 |
| 4,510,704 | 4/1985 | Johnson | 36/136 |
| 4,703,445 | 10/1987 | Dassler | 364/561 |
| 4,814,661 | 3/1989 | Ratzlaff et al. | 73/172 X |
| 4,824,107 | 4/1989 | French | 273/454 |
| 4,855,923 | 8/1989 | Fullmer | 364/468 |
| 4,884,223 | 11/1989 | Ingle et al. | 364/550 |
| 5,113,869 | 5/1992 | Nappholz et al. | 128/696 |
| 5,299,454 | 4/1994 | Fuglewicz et al. | 73/172 |

OTHER PUBLICATIONS

Computerworld; "Computerized Shoe Track Training" Nov. 3, 1986.
PC Magazine; "The Electric Foot", Apr. 14, 1987.
The New York Times; "Puma Receives Patent 4,763,287" Aug. 13, 1988.

*Primary Examiner*—Emanuel T. Voeltz
*Assistant Examiner*—M. Kemper
*Attorney, Agent, or Firm*—Lappin & Kusmer

[57] ABSTRACT

To provide a pair of shoes responsive to the relative forces applied to a wearer's feet, at least one force sensor is provided in each of a left and right shoe. The sensor detects pressures which are then converted from a form provided by the sensor into a digital form which may be processed on by a microprocessor. The processor then executes any one of a number of force analysis programs and outputs, in a preferred form, a force model comprising attack, decay, sustain and release information. Each shoe then transmits coded information representing the sensed force profile to a central receiving device which may be located in a watch-like receiver worn on the wearer's wrist. The receiving device has the ability to pick up and discern signals transmitted by each left and right shoe and also from a number of auxiliary transmitters. Control of the display is made through the use of selector switches which also appear on the user interface. The display also contains its own CPU which controls the display and maintains a record of parameters entered by the user, such as weight. By incorporating the advantages taught in the instant invention, measurements of speed, distance, jump time, and the wear experienced by a pair of shoes, may all be accurately recorded and displayed for the user.

19 Claims, 5 Drawing Sheets

APPARATUS FOR MEASUREMENT OF FORCES AND PRESSURES APPLIED TO A GARMENT

This is a continuation of application Ser. No. 07/975,854 filed on Nov. 13, 1992 now abandoned.

BACKGROUND OF THE INVENTION

This invention relates, generally, to the field of apparel which may be used to provide information of a specific nature to a wearer, and more particularly to a running shoe which employs a force sensor in order to enable a microprocessor located within the shoe to receive data from the force sensor and to perform real time force analysis calculations, so as to permit the display of the results of such calculations on a convenient display device.

By way of background, in recent years, the field of athletics has benefitted greatly from the increased use of electronics in combination with traditional sporting gear and sportswear. In the field of baseball, for example, the radar gun and high speed video camera have been used to measure a pitcher's speed and record a pitcher's motion in an effort to provide coaches with the information needed to perform analysis necessary to train a pitcher to pitch more efficiently and with fewer injuries. Other examples include the use of high technology systems to record the movement of an athlete in, for example, the sports of tennis and golf and to use these records, once again, perform the analysis necessary to improve an athlete's performance while reducing injury.

Coupled with these technological advances has been a desire by each athlete to know as much about his or her personal performance, in as close to real time, as possible so as to enable these athletes to make adjustments to their individual movements and motions while engaging in their particular sport or activity. It has been determined that one area where feedback to the athlete would be most desirable is the area of specialized sports footwear, such as running shoes or sneakers.

In the sport of running, one early attempt to develop a sport shoe which would enable the wearer to get feedback on his or her performance, was the PUMA RS Computer Shoe, a running shoe which contained the circuitry for a simple pedometer coupled with a real time clock. This shoe is described in U.S. Pat. No. 4,771,394 to Cavanagh. As discussed, after an initial shoe training period, runner then uses the shoe by activating the shoe at the beginning of his or her run and then stopping the shoe at the end of the run. After completing the workout, the runner then connects the running shoe to a microcomputer, through a cable, by way of a data port physically molded into the rear of the shoe. Then, by using software running on the microcomputer, the information stored in the shoe during the run (such as time and distance) down loaded across the data port and displayed or available for use in other calculations. In this way, the runner can record, on a daily basis, the distance travelled, speed and time elapsed for each training session.

One obvious disadvantage of such an arrangement is that the runner has to wait until he or she has completed his or her training session before data can be down loaded from the shoe and properly analyzed. Another obvious disadvantage is that the runner must also have access and be near a microcomputer before any data may be analyzed. In addition, since the Cavanagh shoe measures only distance travelled in relation to time, the running shoe of the prior art does not provide the runner with any information which is not also available through more traditional (and less expensive) means. Finally, the Cavanagh shoe is limited to measuring one foot strike (a binary value) at a time. Since this sensed footstrike parameter is binary (either on or off) the only dynamic information available for further processing is time. This is because the Cavanagh shoe does not measure force.

It is noted that the specific use of force sensors moved into specific medical shoes has been noted in an effort to allow technicians to perform the analysis. This work has been performed by the Tech-Scan company of Boston, Mass. However, in this case each sensor was hard wired directly to an outboard computer, rendering its application inappropriate to the needs of the present invention.

Accordingly, it has been determined that the need exists for an improved running shoe which may be used to measure the force applied to the sole of a running shoe, and then transmit force profile information from each of the left and right shoes, without the use of interconnecting wires, to a small display device which may be worn, like a watch, on the athlete's wrist. By carefully measuring, transmitting and displaying such force profile information from each foot, an improved running shoe is provided which, in addition to measuring foot strike and providing associated pedometer functions, may also be used to measure and display the force profile sustained by a wearer's foot for the purposes of training as well as for the purposes of monitoring shoe wear.

SUMMARY OF THE INVENTION

Generally speaking, in accordance with the invention, an improved force analysis shoe is provided which is adapted to be responsive to the force applied to the sole of a wearer's running shoe, and then convert this force related information into a form which may ultimately be transmitted to a display device worn by the user. In practice, at least one force sensor is provided in each left and right shoe. Each force sensor is then, in turn, connected to appropriate conversion and processing circuitry to convert the sensed force information into a data stream which may be transmitted to a data receiver. The data stream from each running shoe is uniquely identified so that left and right shoes can be identified and so that interference from nearby shoes, such as might occur during a race, can be minimized.

Although many configurations are possible under the invention, it is preferable that in operation, force information be transmitted from each shoe to the wearer's display device as a value representing at least a portion of a pre-defined force envelope. Analysis of the force envelope first takes place within the shoe, and then data representing the elements of the identified force envelope are transmitted to the users display, where it is compared to information pre-stored in a look-up table, and finally displayed.

It is anticipated that some uses for the improved force analysis shoe will be to measure, in a training mode, distance and speed more reliably and accurately than possible in the prior art. In addition, more complex measurements and analysis of the forces applied to a foot during sport will also be possible. The improved force analysis shoe will also be useful in measuring the time that a wearer remains airborne, with both feet in the air, known in the sport of basketball as "hang-time". It is also anticipated that, by permanently storing within the shoe a measure of forces applied to the wearer's shoe over the life of the shoe, the actual compression of the shoe materials, as well as other wear factions, may be calculated thereby providing an indication of when the shock absorbing properties of the shoe may be worn out.

Accordingly, it is an object of the invention to provide an improved force analysis shoe.

It is another object of the invention to provide an improved force analysis shoe wherein the force absorbed by each shoe is measured and processed separately in each shoe, and wherein data, representing the force envelope measured in each shoe is transmitted separately to a display device worn by the shoe wearer.

It is a further object of the invention to provide an improved force analysis shoe which, in combination with a display device, may display the wearer's speed, or distance travelled, or "hang-time" spent with both feet in the air.

It is still another object of the invention to provide an improved force analysis shoe wherein said force measurement is recorded for the life of each shoe to provide an indication to the wearer of the physical condition of the shoe and its remaining shock absorbing properties.

It is still a further object of the invention to provide an improved force analysis shoe which is light-weight, balanced from left to right foot, and which suffers no performance degradation over a traditional athletic shoe.

It is yet another object of the invention to provide an improved force analysis shoe in which information is conveyed between the shoe and a data display device, wherein no physical connection is required between the shoe and the data display device.

It is yet a further object of the invention to provide an improved force analysis shoe in which additional inputs from other sensors, such as those which may be connected to measure heart rate or body temperature, may also be combined with the information received from each shoe and then used in calculations and/or displayed on the data display device.

Still other objects and advantages of the invention will, in part, be obvious and will, in part, be apparent from the specification.

The invention accordingly comprises the features of construction, combination of elements and arrangements of parts which will be exemplified in the constructions hereinafter set forth, and the scope of the invention will be indicated in the claims.

BRIEF DESCRIPTION OF THE DRAWINGS

For a fuller understanding of the invention, reference is had to the following descriptions, taken connection with the accompanying drawings, in which.

DETAILED DESCRIPTION OF THE PREFERRED EMBODIMENTS

Figure 1:
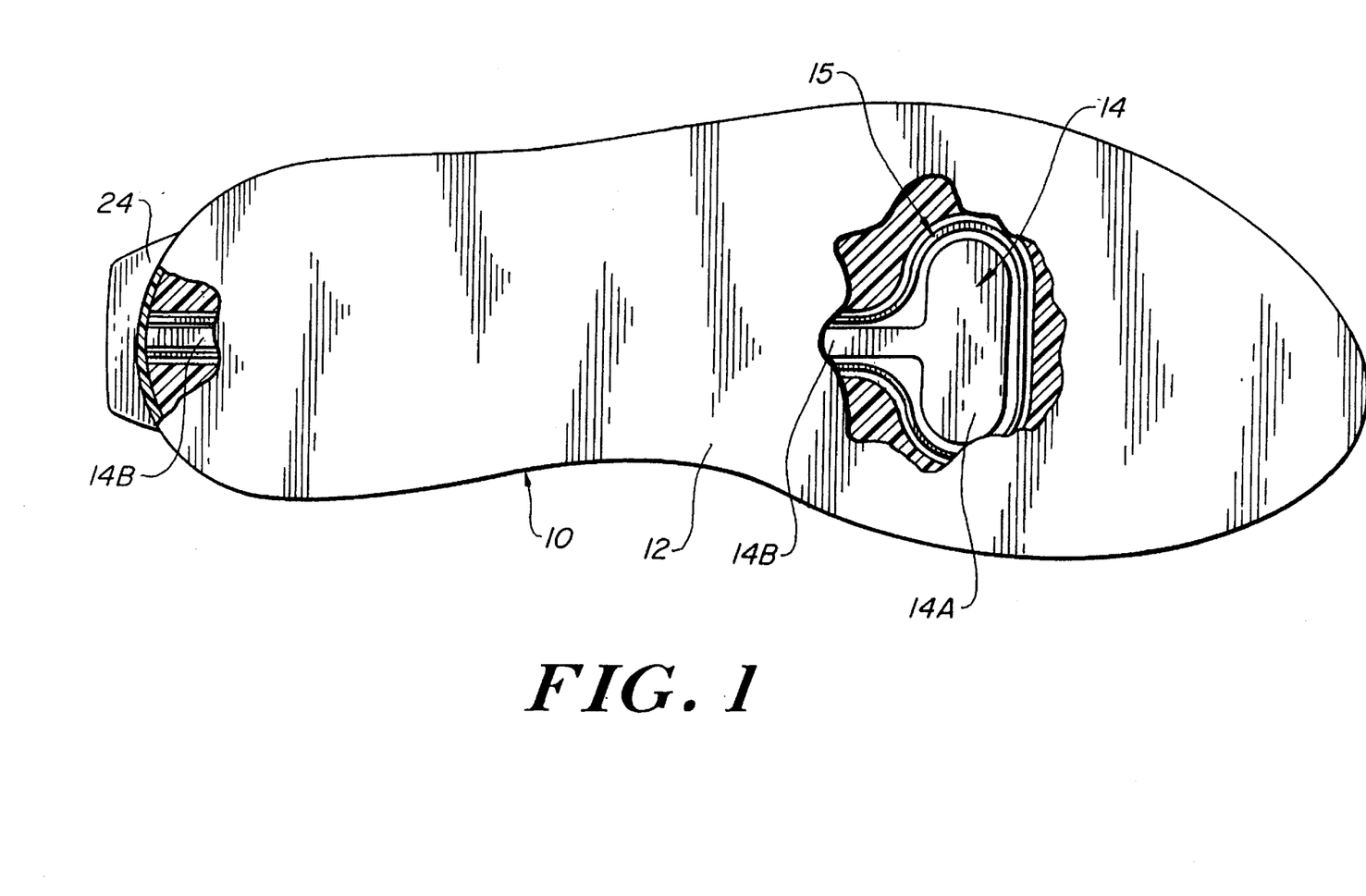
FIG. 1 is a cut-away bottom view of a running shoe constructed in accordance with a preferred embodiment of the invention.

Referring first to FIG. 1, a cut-away bottom view of a running shoe constructed in accordance with a preferred embodiment of the invention is shown. The shoe, generally referred to as 10, is manufactured according to a well-known design using well-known construction techniques. However, unique to the construction of the running shoe fabricated in accordance with the instant invention is the inclusion of a force sensor 14 located proximately to the ball of the wearer's foot. As can be seen more clearly in FIG. 2, force sensor 14 is sandwiched between the layers of material which comprise the outer sole 12 of the running shoe 10 or that portion which makes direct contact with the ground, and the inner sole (not shown) which the wearer directly contacts with his or her sock. Force sensor 14 is an integral unit, and is designed to generate an output signal relative to the pressure applied to its active surface. One example of a sensor which may be used as force sensor 14 is the model number E050 manufactured by Interlink Electronics Co., Carpenteria, Calif.

Figure 5:
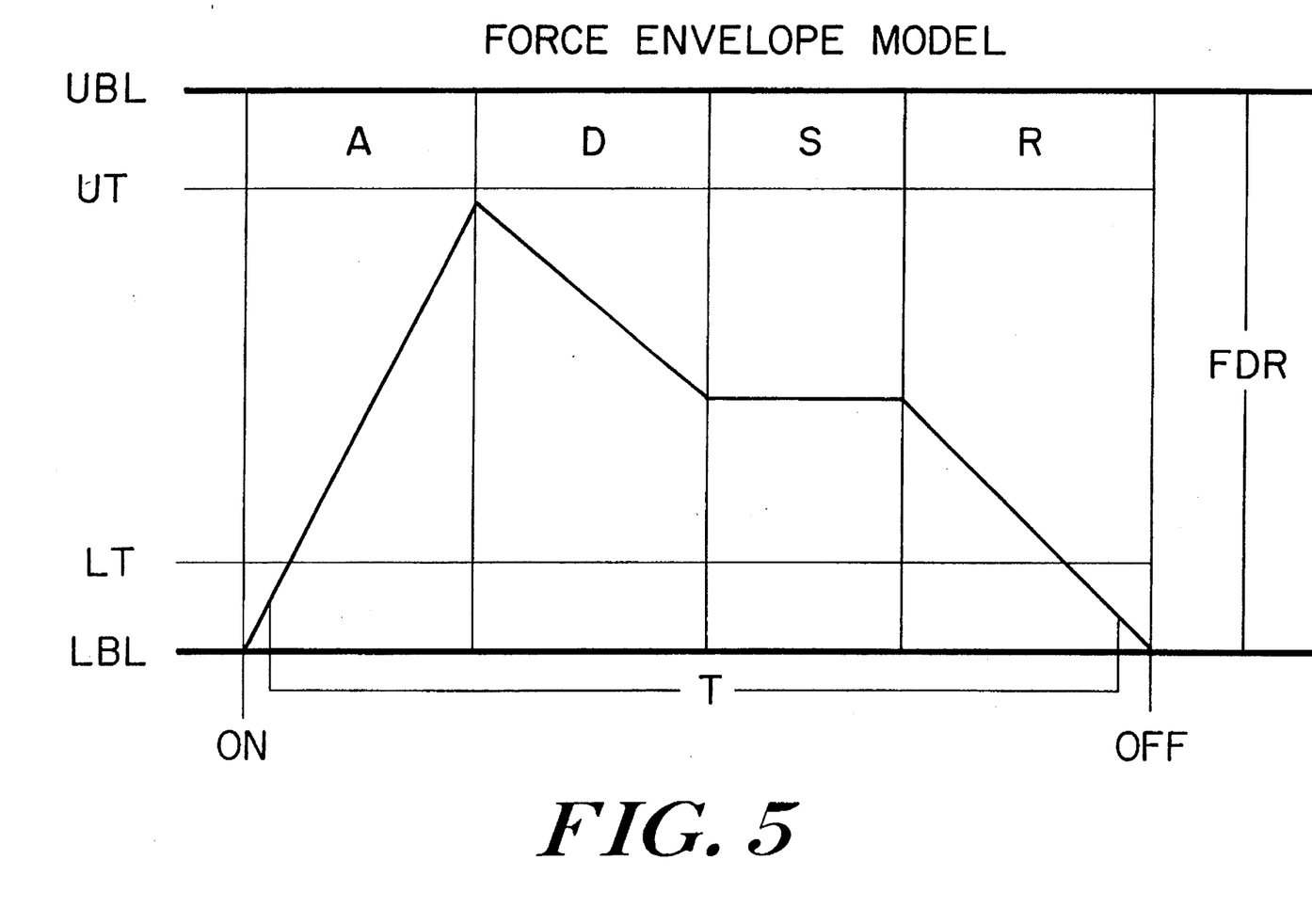
FIG. 5 is chart modeling the force envelope which is sensed, transmitted and displayed to the user in accordance with a preferred embodiment of the invention.

As noted above, force sensor 14 is responsible for detecting the pressure exerted against the sole of a wearer's shoe during a physical activity. Although only one sensor is shown for each shoe, it is noted that it may also be desirable to detect force location, as well as magnitude, by employing multiple sensors. It has been determined that qualities of force sensor 14 which must be considered during design are its size, sensitivity, shape and placement. It is not expected, or desired, that force sensor 14 carry the entire pressure applied to the base of the shoe. Instead, force sensor 14 should be situated such that it may be responsive to a representative amount of force conveyed to force sensor 14 across the sole of the shoe. Thus, by controlling size, shape and placement of sensor 14, force information to be sensed and measured may easily be obtained. As may be easily noted, the sensitivity of force sensor 14 will be determined by the above parameters and by the nature of the construction of the force sensor. Therefore, since force sensor 14 will provide a continuous output of force, information, it has been determined that the data generated by sensor 14 can best be processed when it is used to generate a force envelope having discrete components which, together, may model various physical events affecting the shoe. Therefore, such a model will be described in more detail when the force envelope model of FIG. 5 is discussed infra.

Figure 2:
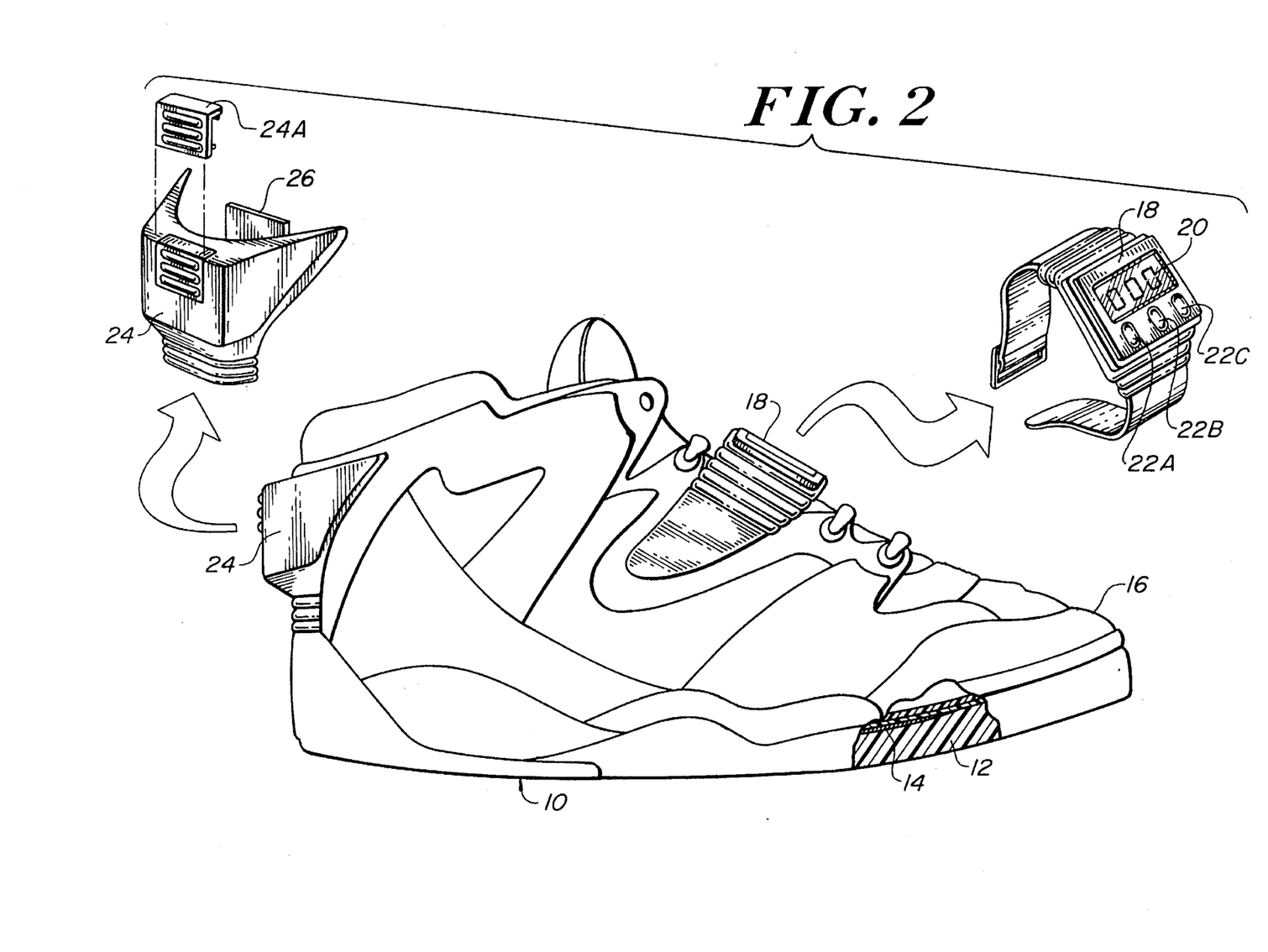
FIG. 2 is a cut-away side view of a running shoe constructed in accordance with a preferred embodiment of the invention.

Returning once again to the construction of shoe 10, force sensor 14 is further characterized by defining a pressure sensitive area 14A and an flexible lead tail 14B. As illustrated in FIG. 1 and FIG. 2, flexible lead tail 14B extends from the base of pressure sensitive area 14A and is located between the layers of material which comprise the construction of the sole of the running shoe. A processor and transmitter module 26 (shown in FIGS. 2 & 3), which contains the circuiting necessary to process the data received from force sensor 14 and then transmit force envelope data to a data display device, is preferably located near the rear heel area of shoe 10 within housing 24. In practice, processor and transmitter module 26 may be designed around an Intel 80 C550 processor, which incorporates a UART, ROM, RAM and an A/D converter. In operation, flexible lead tail 14B connects the pressure sensitive area 14A of force sensor 14 to processor and transmitter module 26. The sole of shoe 10 also incorporates a transmitting antenna (not shown), which is coupled to processor and for transmitter module and surrounds force sensor 26.

As may be well understood, force sensor 14 is a key component of the instant invention, and is responsible for sensing the force, or pressure, which is applied to the sole of the wearer's shoe. This pressure is created by the weight of the wearer and changes in relation to the physical actions or motion of the wearer. As noted above, force sensor 14 is embedded into the sole 12 of shoe 10 in such a manner that it may respond to a range of pressures and forces associated with for example, a wearer standing still, a wearer having his or her foot in mid-air, and a wearer coming down from a high jump. Because of this wide range of possible inputs, it is recognized that it is important to locate force sensor 14 within the sole 12 of shoe 10 in such a manner and position that it may be responsive to all those pressures which are desired to be sensed. Since force sensor 14 is, itself, quite durable, it may be molded or glued into place using a variety of well-known techniques.

Finally, as can be seen in FIG. 2, processor and transmittal module housing 24 which house processor and transmitter 26 is also disposed proximate to the heel area of shoe 10. If desired, housing 24 may also be provided with an access panel (not shown), which may be used to service and adjust processor/transmitter module 26.

Figure 3:
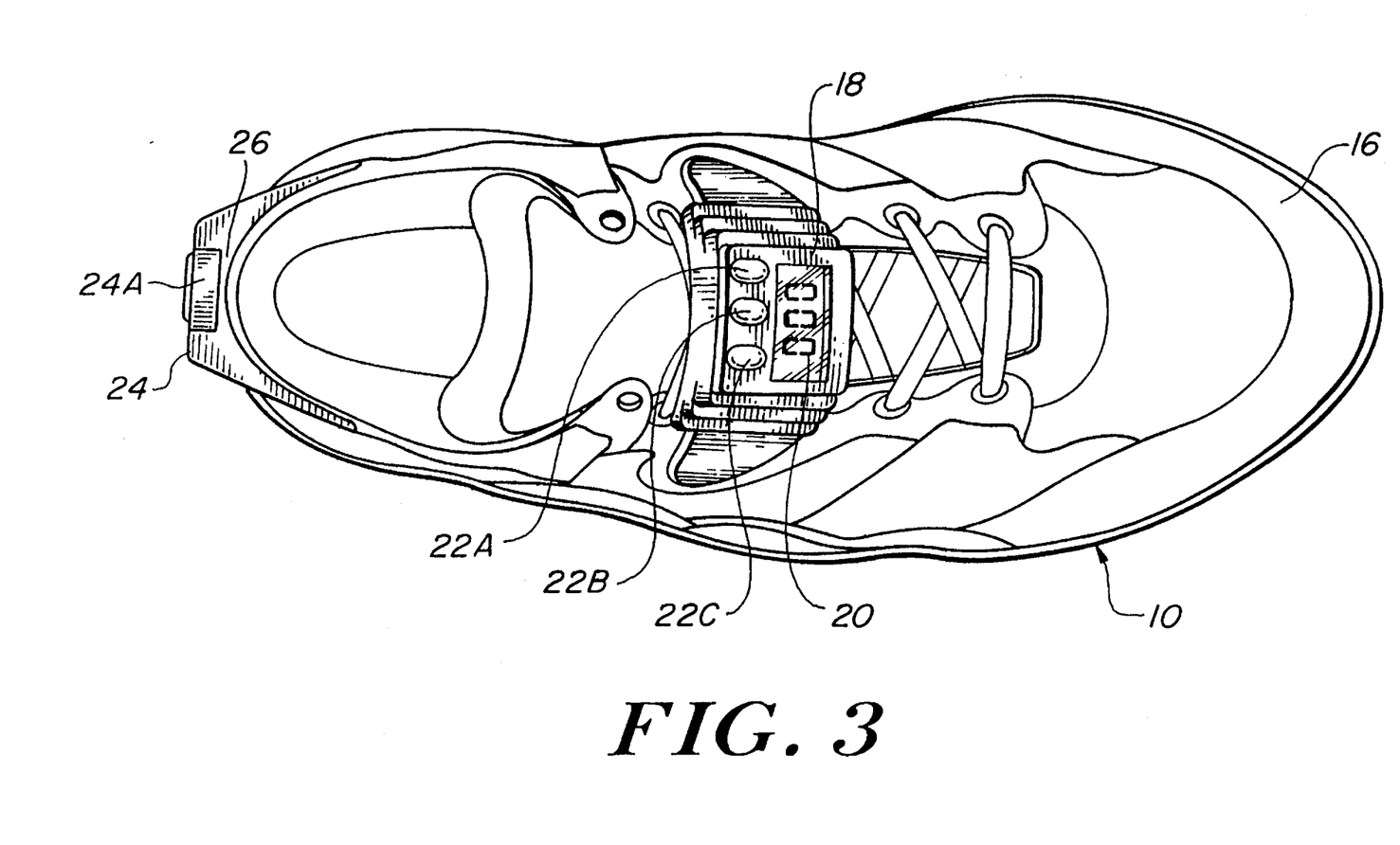
FIG. 3 is a top view of a running shoe constructed in accordance with a preferred embodiment of the invention.

Referring next to FIG. 3, a top view of a running shoe 10 constructed in accordance with a preferred embodiment of the invention is shown and generally indicated as 16. The top 16 of the running shoe 10, like the sole 12, is manufactured according to a well known design. However, in one embodiment, the lacing area of shoe 10 may be modified to support a display module 18 which functions as a user interface to the invention. Preferably, display module 18 comprises a display panel 20, and a plurality of switches 22A, 22B and 22C each of which, either alone or in combination, may be used to adjust the display into a preferred operating mode. Display module 18 may be secured to the lace area of either the left or right running shoe. In addition, as can be seen in FIG. 2, by using a releasable securing mechanism, such as the hook-and-eye fastening material Velcro®, display module 18 may be adapted to be removed from the lacing area of shoe 10, and secured, for examples, around the wearer's wrist in the manner of a traditional watch band.

As discussed above, it is intended that the force analysis shoe be designed to monitor the pressure profile of the forces applied to a wearer's foot and then to display various desired information to the wearer based upon this force profile. Therefore, by using force sensor 14 located in the sole of each left and right shoe, the forces applied to the sole of the left and right shoes may be easily sensed and processed with the resulting data being relayed to display module 18 for further processing and display.

Figure 4:
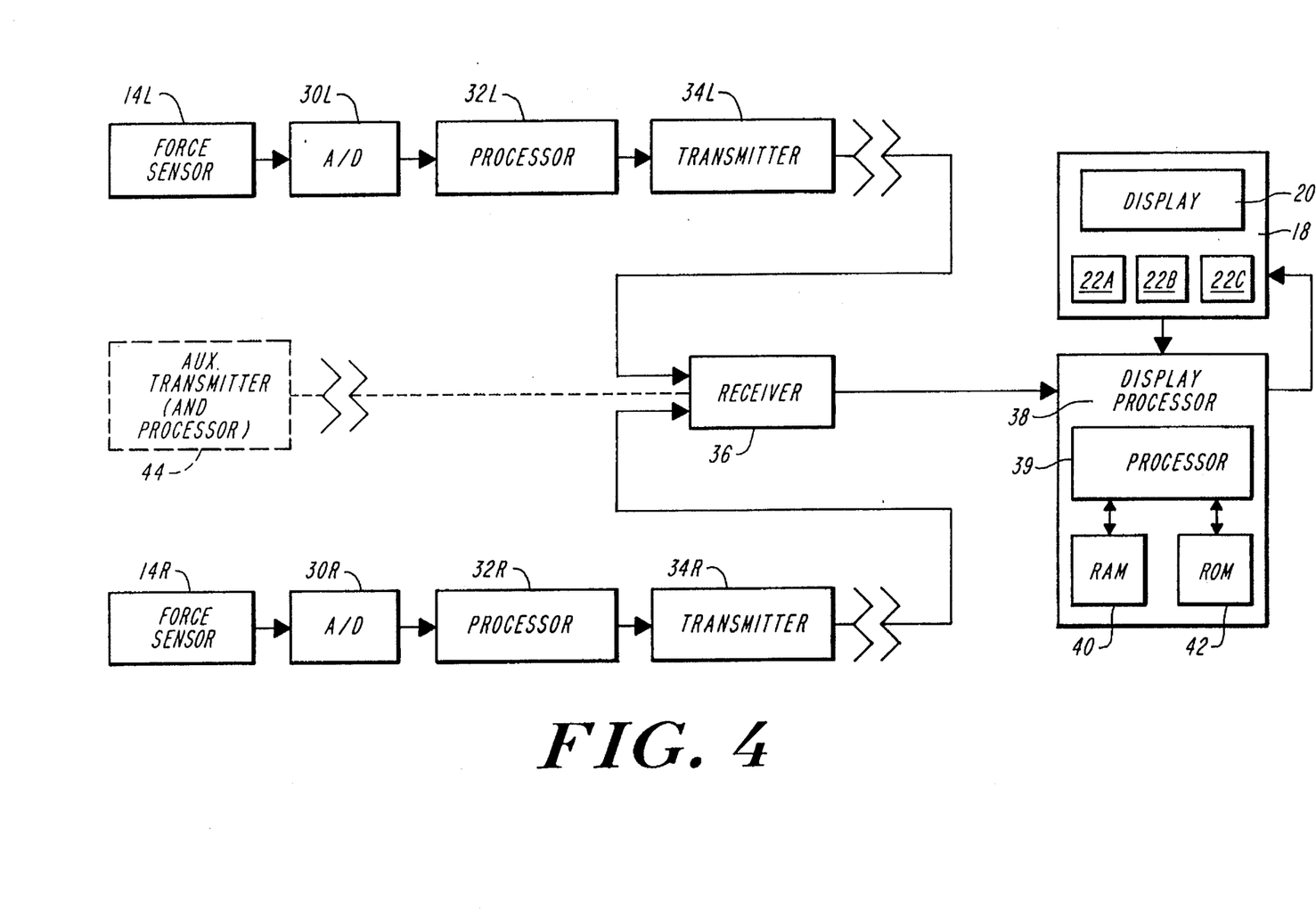
FIG. 4 is a block diagram illustrating the construction of a preferred embodiment of the invention.

Referring then to FIG. 4, a block diagram illustrating the construction of a preferred embodiment of the instant invention is shown. As noted supra, the system is designed to receive information alternately from a left and right shoe. Thus, construction of the left shoe and the right shoe of the invention are matched and applicable components duplicated. However, for the purposes of this description, only the right shoe will be described.

Starting from the left hand side of FIG. 4, and with reference to the construction described above and shown in FIGS. 1, 2 & 3 above, the sensed input to the invention comes from force sensor 14R which responds to pressure applied to the sole of the user's right foot. This pressure is converted into an electrical signal which is then conducted through flexible lead tail 14B to processor/transmitter module 26 located near the rear heel area of shoe 10. Processor/transmitter module 26 comprises an analog to digital converter (A/D) 30R which is used for translating the analog pressure information developed by force sensor 14R into a digital signal which may be more easily manipulated. The output of A/D 30R is then coupled to a processor 32R which, as noted above, is preferably of the type similar to the Intel 80C550, which incorporates RAM, ROM, a UART, and which may also include the A/D function of A/D 30R. Processor 32R receives data from sensor 14R and then uses such data to calculate a force profile based on a force envelope model, to be discussed infra. Processor 32R then outputs a series of values representative of the current force envelope model, and these values are transmitted by transmitter 34R so that the current force envelope can be recreated and displayed on display 20. This is desirable since the data output by processor 34R is transmitted to receiver 36 via a wireless method, and at the present time, it is easier (though not impossible) to transmit data via a wireless method in serial rather than parallel form.

As noted, the output of processor 32R is coupled to a transmitter 34R which transmits force profile data to receiver 36. It is desirable that the format of the data transmitted by right foot transmitter 34R and corresponding left foot transmitter 34L include a unique identifying signal so that receiver 36 is able to distinguish a signal arriving from the right foot from a signal arriving from the left foot. It is also desirable that each shoe and each pair of shoes be uniquely identified so that signals from other shoes in close proximity to receiver 36 will be ignored. Such filtering is important when many runners wearing similar shoes are in close proximity to each other, such as may occur during a race.

Continuing with the description, the output of receiver 36 functions as an input to display processor 38. Display processor is also a general purpose microprocessor 39 such as an INTEL 80C550, and also comprises RAM 40, used for storing operating parameters which may be changed by the user, and ROM 42, which functions as a look-up table for receiving the parameters of the force envelope model transmitted from microprocessor 39, and then using the parameter to recreate the force envelope. Display processor 38 is then connected to a display device 18 which comprises a display unit 20 and a series of input switches designated 22A, 22B and 22C.

In general, display unit 20 is of the liquid crystal display (LCD) type. Such displays have low power consumption and are easy to see in bright light. In addition, it is easy to create cost effective custom LCD displays for indicating information other than numbers.

Input switches 22A, 22B and 22C are responsible for setting the operating parameter of display processor 38. Although three switches are designated at the present time, modifications to the input panel may be made without deviating from the sum and substance of the instant invention.

As can also be seen in FIG. 4, although the instant invention is described as taking an input only from a left and right shoe, it is anticipated that the invention may receive input from other sensors. Auxiliary transmitter 44 may be connected to a number of different sources, including monitors measuring the wearer's heart rate, body temperature, air temperature, respiratory rate, etc. Since receiver 36 will operate generally as a wireless receiver, no physical connection need be made between auxiliary transmitter 44 and receiver 36. It is anticipated that signals from the shoes and other devices may be separated into classes such as class I-left foot, class II-right foot, class III-heart monitor. This may be done to ease transmission and so that receiver 36 may more easily and readily process incoming data. In this way, a large number of input devices may be connected to receiver 36 without being subject to the physical limitations normally found in incorporating a large number of input ports on a small device.

Turning next to FIG. 5, a description of the force envelope model upon which the invention is based will now be described. As illustrated in FIG. 5, the force envelope model is comprised of several distinct parameters and is effectively defined by the data collected by force sensor 14.

The first force parameter is the attack parameter designated as comprising the region "A". Attack parameter "A" represents the initial application of force to force sensor 14. Attack parameter "A" is generated when the sole of the shoe initially hits the ground. By analyzing the characteristic slope and shape of the attack parameter, information regarding the shock absorption capability of the shoe, and the physical condition of the wearer may be obtained.

The second force parameter is the decay parameter designated as comprising the region "D". Decay parameter "D" represents the decay of the force applied to force sensor 14 after the initial attack "A." Decay parameter "D" is generated as the force applied to the sole of the shoe decreases in fact, or remains constant and the structure of the shoe and the wearer's foot begin to absorb a portion of the initial attack. Combined with the attack parameter "A", decay parameter "D" indicates the nature of how hard a wearer has hit his or her foot against a surface and the extent, if any, of rebound.

The third force parameter is the sustain parameter designated as comprising the region "S". Sustain parameter's is generated as the force applied to the sole of the shoe, and the resulting forces acting within the shoe and foot, stabilize. Sustain parameter "S" provides an indication of the steady state force applied to force sensor 14 after the wearer's foot has made contact with the ground, and may be used to gauge the weight and relative force generated by the wearer during movement.

Finally, the fourth force parameter is the release parameter, designated as comprising the region "R". Release parameter "R" is generated as the force applied to the sole of the shoe begins to decrease. Release parameter "R" provides an indication of the wearer's foot leaving the ground in preparation for the next step or movement, and may be used to determine speed by comparing multiple releases to stride length and time.

While each of these parameters may be evaluated individually, they may also be considered together, yielding force profile characteristics which may be used to identify specific actions or activities. In operation, the data provided by the force sensors to processor/transmitter module 26 is analyzed and a force profile is created. Then a series of reference points describing the instant profiles is transmitted by processor/transmitter module 26 to the display module 18. The display processor 38 of the display module is then comparing the received reference points and compares them to force profile reference points pre-stored within its internal ROM. Such comparison permits the display processor 38 to recreate relevant force profile information and then display the desired results on display 18.

In order to further understand such force profile characteristics, we must define reference points to the environment in which the force envelope exists. These reference points are shown in FIG. 5 and are described as follows:

UBL and LBL define the operational limits of force sensor 14, and serve as an upper baseline and lower baseline;

FDR describes the full dynamic range of force sensor 14 which may need to be scaled mechanically and electrically in order to limit the output of the sensor so that it more accurately matches the range of forces expected to be generated by the wearer;

Upper threshold UT and lower threshold LT provide an indication of excessive force and, in addition, lower threshold LT may also be used to determine when the wearer's foot is located on the ground and not in the air;

ON and OFF parameters indicate the time when force is applied to the sensor and when force is removed from the sensor; and The T parameter indicates the duration of the force envelope which is used in determined statistics such as speed, stride type, lapsed time, or jumping time.

Operation of the invention will now be described with reference to a sample embodiment. In operation, a user will put on a pair of running shoes each containing at least one sensor and the associated electronics defined in the instant invention. No on/off switch is necessary, since through the use of software, an indication of no pressure on either shoe for an extended period of time will indicate that the wearer has taken the shoes off or is in a position where the wearer's feet are both off the ground for an extended period of time, such as reclining. Once any sensor detects the application of force, that force will be converted into a digital representation by A to D 30R or 30L. After processing by processor 32R or 32L, a digital data stream representing a coded version of the sensed force profile will be generated. The digital data stream will then be combined with a unique digital shoe signature and transmitted by transmitter 34A or 34L to receiver 36. Receiver 36 will then relay the coded force profile information to CPU 38 which will, after performing the desired data manipulations, indicate on display 20 of display device 18 that the system is functioning and operational, and then display the results of the calculations. At this point, the wearer may use the input selector switches 22A, 22B and 22C to set the desired mode of operation and operating parameters. One such possible operating parameter would be the measure of "hang time". Hang time is a common vernacular for the time spent in the air with both feet off the ground. Such measurement is particularly important in the sport of basketball where successful athletes are capable of running and jumping quite high, remaining suspended off the ground for extend periods of time. By measuring the force sensed in both shoes and noting when both shoes have left the ground, the invention may calculate the difference in time between the last shoe leaving the ground and the first shoe hitting the ground again, thereby displaying this difference in time as "hang time". This hang time information may then be stored and later compared with other information previously stored.

In another application of the instant invention, by measuring the cadence that a wearer provides to each shoe, an electronic pedometer may be developed which measures the distanced travelled and speed taken to complete the distance.

Another important function available with the instant invention, and not available in the prior art, is the development of a "wear monitor". As is well known, the shock absorbing characteristics of materials used in running shoes have a finite effective life. This life span often ends before material of the shoe looks worn out to the wearer. Thereafter, potential physical damage or injury may result from running in shoes that no longer provide the proper amount of shock absorption protection.

The effective life of the material used in the manufacture of a shoe can be calculated as a function of the amount of force or pressure exerted on it over time. This net accumulated force eventually wears out the effectiveness of the shock absorbing material. Since manufacturers often do extensive testing on materials used in the manufacture of their shoes, it is possible to get a rating from the manufacturer which can then be programmed into processor/transmitter module 26. Thereafter, as the wearer wears the shoe, information relating to force may be subtracted from the overall life expectancy of the shoe thereby providing an indication to the wearer when the shock absorbing properties of the shoes have expired.

Although in the instant invention it is described that force sensor 14, A to D converter 30R and 30L, processor 32R and 32L and Transmitter 34R and 34L all are located within the shoe and that Receiver 36, display processor CPU 38 and Display 18 all are located within an external display device, it can be easily understood that, if desired, analysis functions may be performed either within the shoe or the display. While, in the preferred embodiment, values used to define the force envelope are transmitted by transmitter 34R and 34L to receiver 36, reducing the size and complexity of the receiver and associated CPU and display, other configurations are also possible. Such a change is simply a design choice which will depend upon the cost, size and weight of components available at the time of manufacture of the shoe. However, the advantage obtained from the instant invention over the prior art is realized particularly by measuring the force applied to each of the wearer's shoes, and transmitting such data transmission from each shoe to a central data display point. It is also anticipated that while wireless transmission of data from each shoe to the central receiver is optimal, in some instances, wired connection from each of the shoes to a central receiver may also be desirable.

It is noted that since the invention, and resulting force profile information, is designed to be useful to people, men and women, of many different weights, the weight of the user must be known before the display of force profile information can take place. Therefore, the invention anticipates that the weight of the user will be set and then stored in the display processor by use of the data input switches.

It is also noted, as briefly described above, that the architecture of the invention permits the receiver and display processor to accept signals not only from the user's shoes, but also from many other different signal sources, such as other "smart" exercise equipment and health monitors. Therefore, an important aspect of the invention is that the receiver and display processor are able to distinguish among signals generated by the user's shoes and other external devices, such as force profile signals, may be processed first. On the other hand, by assigning different signal "classes" to each signal generating device, it is possible to identify the source of an incoming signal so that, for example, should the above noted heart monitor be transmitting an indication that the user's heart rate is higher than an acceptable limit, then that signal class may take priority over the data being received from the shoe, and may be processed immediately, in order to alert to the user to a dangerous condition.

With respect to the use of the invention in connection with a shoe, the current embodiment shows the invention comprising an integral part of the construction of the shoe itself. However, it is anticipate that the construction of the invention may also be applied to a replacement-type "sock liner", such as the type currently sold by Spectrum Sports of Twinsburg, Ohio. In such a case, the processor would compensate for the change in relative force profile information which would result from the force sensor being located closer to the user's foot and further away from the actual sole of the shoe. In addition, it might also be necessary, depending on cost considerations, to move more of the processing of the force profile data from the sock liner to the display processor. However, such modifications are within the scope of the invention and may be accomplished without deviation from the teachings of the invention.

Finally, while the instant invention is described with relation to a shoe, it is also anticipated that the invention may be utilized without extensive modification, in other sports measuring force applied to other parts of the body. For example, it is anticipated that the installation of force sensors in boxing gloves may be advantageous in allowing a boxer in training to register the force provided by each alternate left and right punch as well as providing a graphic indication the timing, or cadence of each punch thereby providing the boxer with a better feeling for the status of his or her training. It is also anticipated that the instant invention may find value in the sport of golf where a combination of sensors provided in the wearer's shoes as well as the wearer's glove may indicate to the wearer when he or she has shifted his or her weight and how this shift effects their grip on the golf club.

Thus, an apparatus for the measurement of forces and pressures applied to a garment may be provided which effectively meets all of the above desired goals, overcoming the limitations of the prior art.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative, and not in a limiting sense.

It will also be understood that the following claims are intended to cover all of the generic and specific features of the invention, herein described, and all statements of the scope of the invention which, as a matter of language might be said to fall there between.

What is claimed is:

1. A garment comprising, in combination:

at least one individual force sensor physically connected to said garment for sensing each application of force applied to said sensor and for generating a force signal representative of said each application of force to said sensor;

processing means disposed on said garment for processing each said force signal so as to produce a time and intensity profile of said force signal, said profile being characterized in having at least three discrete time segments, and for representing each of said segments of said profile by a value selected from a coded series of reference values, said segments including an attack segment representative of the parameters of the initial application of said force to said garment; a sustain segment representative of the parameters of the continued application of said force to said garment, and a release segment representative of the parameters of the diminution and termination of the force applied to said garment;

means for transmitting said selected values of said coded series of reference values; and means for receiving and decoding the transmitted selected values of said coded series of reference values to recover time and intensity information therefrom for analysis of the physical performance of a wearer of said garment.

2. A garment as set forth in claim 1, wherein said garment is a shoe liner.

3. A garment as set forth in claim 1, wherein said garment is a glove.

4. A garment as set forth in claim 3 wherein said glove is a boxing glove.

5. A garment as set forth in claim 1 wherein said segments also include a decay segment representative of the parameters of decay of said initial application of force.

6. A garment as set forth in claim 1 wherein said garment is footwear comprising at least a sole portion, and said force sensor is disposed proximate said sole portion for sensing each application of force applied to said sensor;

said processing means being disposed on said footwear for processing each said force signal so as to produce said profile of the time and intensity parameters of said force signal said profile being characterized in having at least an attack segment representative of the parameters of the initial portion of said application of said force to said sole portion; a decay segment representative of the parameters of decay of said initial portion of said application of force to said sole portion; a sustain segment representative of the parameters of the continued application of said force to said sole portion, and a release segment representative of the parameters of the diminution and termination of said application of force to said sole portion.

7. A garment as set forth in claim 6 wherein said garment is footwear comprising at least a pair of shoes each having a sole, and said force sensing means comprises a pair of force sensors respectively disposed proximate said sole of each said shoe for sensing forces applied to said soles.

8. Footwear as set forth in claim 6, wherein said force signals applied to said sole portions are accumulated in said processing means over the life of said footwear, and wherein said processing means further comprises means for determining when the total of the accumulated force signals exceeds a predetermined value representative of the useful life of said footwear and for generating a signal indicative that the end of the useful life of said footwear has been reached.

9. A garment as set forth in claim 6 wherein said footwear comprises a shoe liner.

10. A garment as set forth in claim 1 wherein said reference values include the upper and lower operational limits of said force sensing means, upper and lower thresholds between said operational limits of said force sensing means, on and off times of the operation of said force sensing means, and the duration of said force profile.

11. A garment as set forth in claim 1 wherein said means for receiving and decoding includes:

memory means having pre-stored therein data representing a plurality of said force profile segments; and means responsive to said transmitted coded series of reference values for selecting from said data in said memory means said information for said analysis.

12. A garment as set forth in claim 1 including display means for displaying said analysis of the physical performance of a wearer of said garment.

13. A garment as set forth in claim 12 wherein said display means comprises a liquid crystal type display.

14. A garment as set forth in claim 12 wherein said display means comprises a light-emitting diode type display.

15. A garment as set forth in claim 1 wherein said processing means comprises means for adapting the dynamic range of said force sensing means so as adjust the range of said force signals to match the range of said force.

16. A garment as set forth in claim 1 wherein said means for transmitting comprises wireless transmission apparatus.

17. A garment as set forth in claim 1 wherein said force signals are analog signals and said processing means includes analog-to-digital conversion means for converting said analog signals to digital form.

18. A garment as set forth in claim 1 wherein said force sensing means comprises a plurality of sources of said force signals, and including means for coupling unique identification signals to said transmitted coded series of reference values so as to identify said sources and permit said means for decoding to distinguish among several of said sources and to accept or reject selected ones of said reference values based on respective ones of said coupled unique identification signals.

19. A garment as set forth in claim 1, wherein said garment is a shoe.

* * * * *